(12) United States Patent
Romanov et al.

(10) Patent No.: US 9,156,987 B2
(45) Date of Patent: *Oct. 13, 2015

(54) POLYMETHINE COMPOUNDS AND THEIR USE AS FLUORESCENT LABELS

(71) Applicant: Illumina Cambridge Limited, Nr Saffron Walden (GB)

(72) Inventors: Nikolai Nikolaevich Romanov, Nr Saffron Walden (GB); Xiaohai Liu, Nr Saffron Walden (GB)

(73) Assignee: Illumina Cambridge Limited, Nr Saffron Walden (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/635,864

(22) Filed: Mar. 2, 2015

(65) Prior Publication Data

US 2015/0167073 A1   Jun. 18, 2015

Related U.S. Application Data

(63) Continuation of application No. 14/325,103, filed on Jul. 7, 2014, now Pat. No. 8,993,784, which is a continuation of application No. 13/791,150, filed on Mar. 8, 2013, now Pat. No. 8,809,551.

(60) Provisional application No. 61/775,092, filed on Mar. 8, 2013.

(51) Int. Cl.
| | |
|---|---|
| *C07D 209/02* | (2006.01) |
| *C07H 19/04* | (2006.01) |
| *C12Q 1/68* | (2006.01) |
| *B01L 3/00* | (2006.01) |
| *C09B 23/06* | (2006.01) |
| *C07D 209/14* | (2006.01) |
| *C07D 209/60* | (2006.01) |
| *C07H 19/10* | (2006.01) |

(52) U.S. Cl.
CPC .............. *C09B 23/06* (2013.01); *C07D 209/14* (2013.01); *C07D 209/60* (2013.01); *C07H 19/10* (2013.01); *C12Q 1/6869* (2013.01); *C12Q 2563/107* (2013.01)

(58) Field of Classification Search
CPC ...... C09B 23/06; C07H 21/04; C12Q 1/6869; C12Q 2563/107
USPC .......... 548/455; 536/26.6; 435/91.1; 422/430
See application file for complete search history.

(56) References Cited

U.S. PATENT DOCUMENTS

| 6,159,673 A | 12/2000 | Nishigaki et al. |
|---|---|---|
| 6,238,838 B1 | 5/2001 | Gaschler et al. |
| 6,291,203 B1 | 9/2001 | Poot et al. |
| 6,348,599 B1 | 2/2002 | Cummins et al. |
| 8,809,551 B1 * | 8/2014 | Romanov et al. ............. 548/455 |
| 8,993,784 B2 * | 3/2015 | Romanov et al. ............. 548/455 |
| 2008/0044352 A1 | 2/2008 | Beletskii |
| 2012/0088262 A1 | 4/2012 | Dehghani et al. |

FOREIGN PATENT DOCUMENTS

| EP | 1792949 | 12/2006 |
|---|---|---|
| EP | 2130875 | 12/2009 |
| EP | 2251380 | 11/2010 |
| GB | 1020295 | 2/1966 |
| JP | 03105338 A | 5/1991 |
| JP | 06332104 A | 2/1994 |
| JP | 2002226731 | 8/2002 |
| SU | 432166 | 6/1974 |
| WO | 99/40223 | 8/1999 |
| WO | 2005/014723 | 2/2005 |
| WO | 2005/044923 | 5/2005 |
| WO | 2010/121163 | 10/2010 |
| WO | 2013/041117 | 3/2013 |
| WO | 2014/135221 | 9/2014 |

OTHER PUBLICATIONS

Levkoev et al. Zhurnal Nauchnoi i Prikladnoi Fotografii i Kinematografii (1958), 3, 419-26.*
"International Search Report and Written Opinion for Application No. PCT/GB2015/051337", mailed Jul. 16, 2015.
An English Translation of JP-03-105338-A (Kawashima, et al.), 1991. Abstract Only.
An English translation of JP-06-332104-A (Meji, et al.), 1994.
"International Search Report and Written Opinion", PCT/EP2013/054783, Apr. 23, 2013, 17 pages.
Kawashima, JP 03105338, Abstract only, May 2, 1991.
Meji, et al., JP 06332104, Abstract only, Dec. 2, 1994.
Moss, et al., "Pure & Applied Chemistry", vol. 67, No. 8/9, 1995, 1307,1367-1370.
An English Translation of JP-03-105338-A (Kawashima, et al.), 1991.
"Chemical Abstract Registry No. 161800-75-5, indexed in the Registry file on STN CAS Online", Mar. 30, 1995.

* cited by examiner

*Primary Examiner* — Jezia Riley
(74) *Attorney, Agent, or Firm* — Illumina, Inc.; Brent C. Moore

(57) ABSTRACT

The present disclosure relates to new polymethine compounds and their use as fluorescent labels. The compounds may be used as fluorescent labels for nucleotides in nucleic acid sequencing applications.

16 Claims, No Drawings

POLYMETHINE COMPOUNDS AND THEIR USE AS FLUORESCENT LABELS

This application is a continuation of U.S. application Ser. No. 14/325,103, filed Jul. 7, 2014, now U.S. Pat. No. 8,993,784m which is a continuation of U.S. application Ser. No. 13/791,150, filed Mar. 8, 2013, now U.S. Pat. No. 8,809,551, which claims priority to U.S. Provisional Application No. 61/775,092, filed on Mar. 8, 2013, which is hereby incorporated by reference in its entirety.

The present disclosure relates to new polymethine compounds and their use as fluorescent markers. In particular the compounds may be used as fluorescent labels for nucleotides in nucleic acid sequencing applications.

BACKGROUND

Several publications and patent documents are referenced in this application in order to more fully describe the state of the art to which this disclosure pertains. The disclosure of each of these publications and documents is incorporated by reference herein.

Non-radioactive detection of nucleic acids utilizing fluorescent labels is an important technology in molecular biology. Many procedures employed in recombinant DNA technology previously relied heavily on the use of nucleotides or polynucleotides radioactively labelled with, for example $^{32}P$. Radioactive compounds permit sensitive detection of nucleic acids and other molecules of interest. However, there are serious limitations in the use of radioactive isotopes such as their expense, limited shelf life and more importantly safety considerations. Eliminating the need for radioactive labels enhances safety whilst reducing the environmental impact and costs associated with, for example, reagent disposal. Methods amenable to non-radioactive fluorescent detection include by way of non-limiting example, automated DNA sequencing, hybridization methods, real-time detection of polymerase-chain-reaction products and immunoassays.

For many applications it is desirable to employ multiple spectrally distinguishable fluorescent labels in order to achieve independent detection of a plurality of spatially overlapping analytes. In such multiplex methods the number of reaction vessels may be reduced simplifying experimental protocols and facilitating the production of application-specific reagent kits. In multi-colour automated DNA sequencing for example, multiplex fluorescent detection allows for the analysis of multiple nucleotide bases in a single electrophoresis lane thereby increasing throughput over single-colour methods and reducing uncertainties associated with inter-lane electrophoretic mobility variations.

However, multiplex fluorescent detection can be problematic and there are a number of important factors which constrain selection of fluorescent labels. First, it may be difficult to find dye compounds whose emission spectra are suitably spectrally resolved in a given application. In addition when several fluorescent dyes are used together, to generate fluorescence signals in distinguishable spectral regions by simultaneous excitation may be difficult because the absorption bands of the dyes which could be useable for this are usually widely separated, so it is difficult to achieve more or less equal fluorescence excitation efficiency even for two dyes. Many excitation methods use high power light sources like lasers and therefore the dye must have sufficient photo-stability to withstand such excitation.

A final consideration of particular importance in molecular biology methods is the extent to which the fluorescent dyes must be compatible with the reagent chemistries used such as for example DNA synthesis solvents and reagents, buffers, polymerase enzymes and ligase enzymes.

As sequencing technology advances a need has developed for further fluorescent dye compounds, their nucleic acid conjugates and dye sets which satisfy all of the above constraints and which are amenable particularly to high throughput molecular methods such as solid phase sequencing and the like.

Fluorescent dye molecules with improved fluorescence properties such as fluorescence intensity, shape and wavelength maximum of fluorescence band can improve the speed and accuracy of nucleic acid sequencing. Strong fluorescence signal is especially important when measurements are made in water-based biological buffers and at higher temperature as the fluorescence intensity of most dyes is significantly lower at such conditions. Moreover, the nature of the base to which a dye is attached also affects the fluorescence maximum, fluorescence intensity and others spectral dye properties. The sequence specific interactions between the nucleobases and the fluorescent dyes can be tailored by specific design of the fluorescent dyes. Optimisation of the structure of the fluorescent dyes can improve the efficiency of nucleotide incorporation, reduce the level of sequencing errors and decrease the usage of reagents in, and therefore the costs of, nucleic acid sequencing.

Described herein are improved polymethine constructs and their use as bio-molecule labels, particularly as labels for nucleotides used in nucleic acid sequencing. Particular improvements can be seen in the efficiency of labelled nucleotide incorporation and length of sequencing read obtainable using the new fluorescent constructs.

SUMMARY

According to a first aspect this disclosure provides polymethine dye compounds of the formula (I) or mesomeric forms thereof:

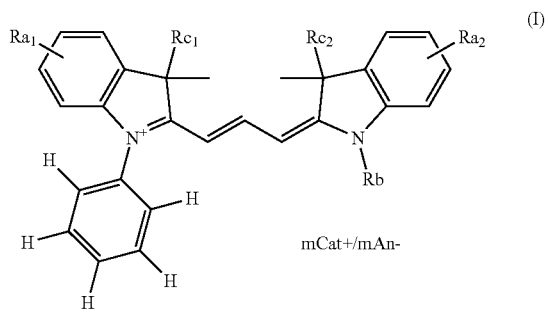

wherein mCat+ or mAn− is an organic or inorganic positively/negatively charged counterion and
m is an integer 0-3;
each of $Ra_1$ and $Ra_2$ is independently H, $SO_2^-$, sulfonamide, halogen, or a further ring fused to an adjacent carbon atom;
Rb is optionally substituted aryl or optionally substituted alkyl;
each of $Rc_1$ and $Rc_2$ is independently alkyl or substituted alkyl; and
either Rb or one of $Rc_1$ or $Rc_2$ contains a linking moiety for further attachment or is linked to a further molecule.

In another embodiment the compounds of the present disclosure can be conjugated with a variety of substrate moieties such as, for example, nucleosides, nucleotides, polynucleotides, polypeptides, carbohydrates, ligands, particles, cells, semi-solid surfaces (e.g. gels) and solid surfaces.

According to a further aspect of the disclosure therefore, there are provided dye compounds comprising linker groups to enable, for example, covalent attachment to such substrate moieties.

According to a further aspect the disclosure provides a nucleoside or nucleotide compound defined by the formula: N-L-Dye, wherein N is a nucleotide, L is an optional linker moiety and Dye is a fluorescent compound according to the present disclosure.

In a further aspect the disclosure provides methods of sequencing using the dye compounds of the present disclosure.

According to a further aspect the disclosure also provides kits comprising dye compounds (free or in conjugate form) which may be used in various immunological assays, oligonucleotide and nucleic acid labelling and for DNA sequencing by synthesis. In yet another aspect the disclosure provides kits comprising dye 'sets' particularly suited to cycles of sequencing by synthesis on an automated instrument platform.

A further aspect of the disclosure is the chemical preparation of compounds of the disclosure.

DETAILED DESCRIPTION

This disclosure provides novel polymethine dye compounds particularly suitable for methods of fluorescence detection and sequencing by synthesis.

According to a first aspect the disclosure provides polymethine dye compounds of the formula (I) or mesomeric form thereof:

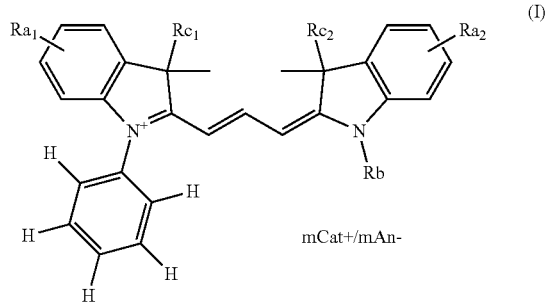

(I)

wherein mCat+ or mAn– is an organic or inorganic positively/negatively charged counterion and
m is an integer 0-3;
each of $Ra_1$ and $Ra_2$ is independently H, $SO_2^-$, sulfonamide, halogen, or a further ring fused to an adjacent carbon atom;
Rb is optionally substituted aryl or optionally substituted alkyl;
each of $Rc_1$ and $Rc_2$ is independently alkyl or substituted alkyl; and
either Rb or one of $Rc_1$ or $Rc_2$ contains a linking moiety for further attachment or is linked to a further molecule.

Each $Ra_1$ or $Ra_2$ can be independently H, $SO_3^-$, sulphonamide, halogen, or a further ring fused to an adjacent carbon atom. $Ra_1$ or $Ra_2$ can be H. $Ra_1$ or $Ra_2$ can be $SO_3^-$. $Ra_1$ can be different to $Ra_2$, for example the structure can have a single sulfonic acid group at $Ra_1$, and H as $Ra_2$. $Ra_1$ or $Ra_2$ can be sulphonamide. The sulphonamide can be $SO_2NH_2$ or $SO_2NHR$, where R is an alkyl, substituted alkyl, aryl or substituted aryl group.

$Ra_1$ or $Ra_2$ can be a further aliphatic, aromatic or heterocyclic ring fused to an adjacent carbon of the indole ring. For example, in such cases when an aromatic ring is fused the dyes end group can represent a structure of type

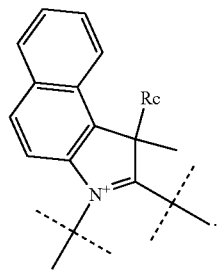

Thus the dyes of the disclosure can be described by Formula (1A), (IB) or (IC):

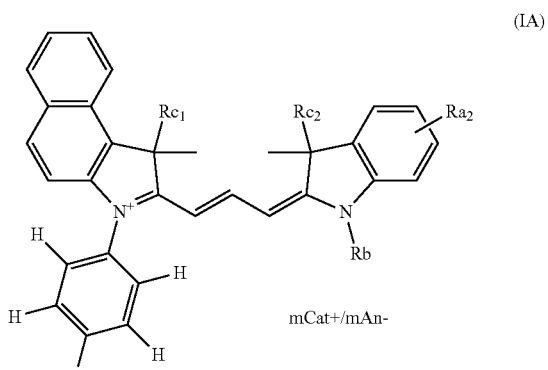

(IA)

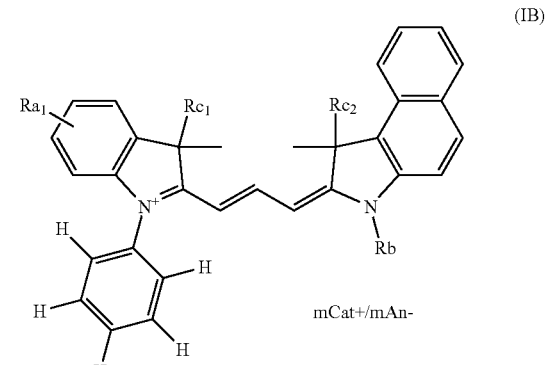

(IB)

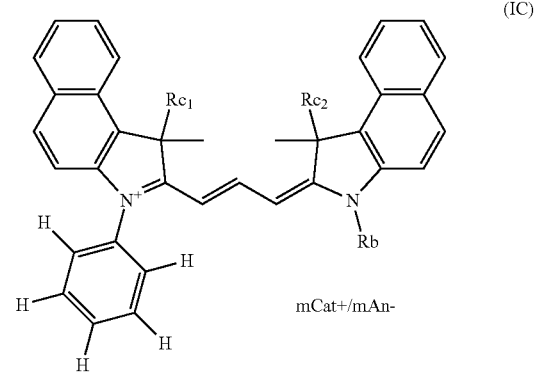

(IC)

In formula (IA), (IB) and (IC) one or both additional rings fused to an adjacent carbon atoms of the indole ring may be optionally substituted, for example with sulfonic acid or sulphonamide.

The compound may be where one of the Ra groups is a further fused ring forming a structure of formula (II):

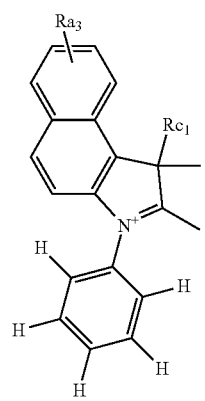

(II)

wherein $Ra_3$ is H, $SO_3^-$, sulphonamide or halogen; and $Rc_1$ is alkyl or substituted alkyl.

Rb can be optionally substituted aryl or optionally substituted alkyl. Rb can be alkyl. Rb can be methyl, ethyl, propyl, butyl, pentyl or hexyl. The alkyl chain can be further substituted, for example with carboxy or sulfonic groups. The Rb can be used for further conjugation. For example if Rb contains a COOH moiety, this can be conjugated with further molecules in order to attach the label. In the case of biomolecule, protein, DNA labelling and suchlike, the conjugation can be carried out via Rb. Rb can form amide or ester derivatives once the conjugation has occurred. The compound may be attached to a nucleotide or oligonucleotide via Rb.

Rb can be aryl or substituted aryl. Rb can be phenyl.

Each $Rc_1$ and $Rc_2$ can be independently alkyl or substituted alkyl. $Rc_1$ and $Rc_2$ may be methyl, ethyl, propyl, butyl, pentyl, hexyl or $(CH_2)_qSO_3H$, where q is 1-6. q may be 1-3. $Rc_1$ and $Rc_2$ may be a substituted alkyl group. $Rc_1$ and $Rc_2$ may contain a COOH or —$SO_3H$ moiety or their ester or amide derivatives.

Either Rb or $Rc_1$ or $Rc_2$ contains a linking moiety for further attachment or is linked to a further molecule. Rb or $Rc_1$ or $Rc_2$ may contain a carboxy or carboxylate (COOH or COO$^-$) moiety. Once conjugated has occurred, Rb or $Rc_1$ or $Rc_2$ may contain an amide or ester.

Examples of compounds include:

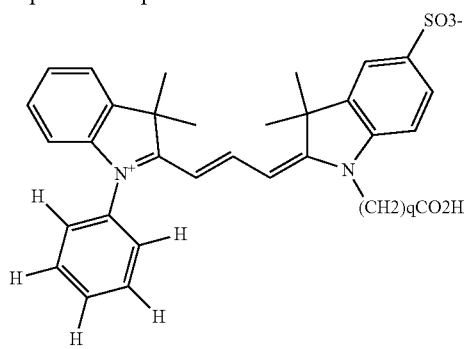

q = 1-5

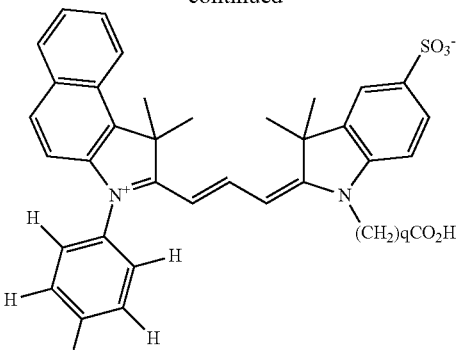

q = 1-5

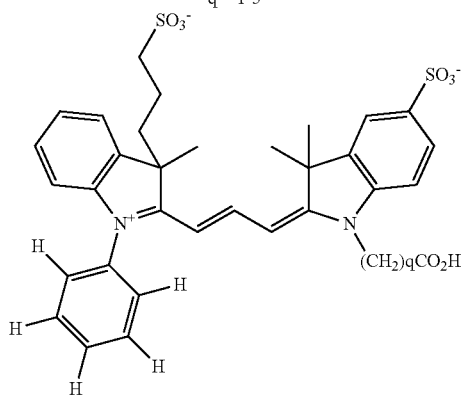

q = 1-5

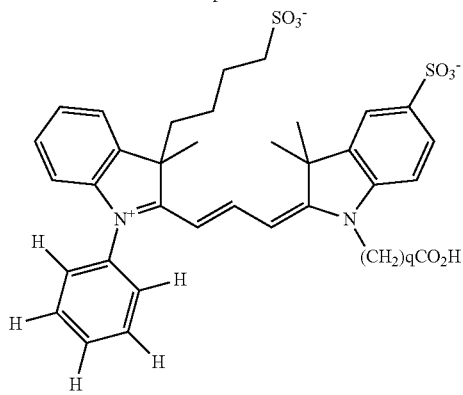

q = 1-5 or salts thereof.

A particularly useful compound is a nucleotide or oligonucleotide labelled with a dye as described herein. The labelled nucleotide or oligonucleotide may have the label attached via substituted alkyl group Rb or $Rc_1$ or $Rc_2$. The labelled nucleotide or oligonucleotide may have the label attached to the C5 position of a pyrimidine base or the C7 position of a 7-deaza purine base through a linker moiety.

The labelled nucleotide or oligonucleotide may also have a blocking group covalently attached to the ribose or deoxyribose sugar of the nucleotide. The blocking group may be attached at any position on the ribose or deoxyribose sugar. In particular embodiments, the blocking group is at the 3' OH position of the ribose or deoxyribose sugar of the nucleotide.

Provided herein are kits including two or more nucleotides wherein at least one nucleotide is a nucleotide labelled with a compound of the present disclosure. The kit may include two or more labelled nucleotides. The nucleotides may be labelled with two or more fluorescent labels. Two or more of the labels may be excited using a single excitation source, which may be a laser. For example, the excitation bands for the two or more labels may be at least partially overlapping such that excitation in the overlap region of the spectrum causes both labels to emit fluorescence. In particular embodiments, the emission from the two or more labels will occur in different regions of the spectrum such that presence of at least one of the labels can be determined by optically distinguishing the emission.

The kit may contain four labelled nucleotides, where the first of four nucleotides is labelled with a compound as disclosed herein. In such a kit, the second, third, and fourth nucleotides can each be labelled with a compound that is optionally different from the label on the first nucleotide and optionally different from the labels on each other. Thus, one or more of the compounds can have a distinct absorbance maximum and/or emission maximum such that the compound(s) is (are) distinguishable from other compounds. For example, each compound can have a distinct absorbance maximum and/or emission maximum such that each of the compounds is distinguishable from the other three compounds. It will be understood that parts of the absorbance spectrum and/or emission spectrum other than the maxima can differ and these differences can be exploited to distinguish the compounds. The kit may be such that two or more of the compounds have a distinct absorbance maximum above 600 nm.

The compounds, nucleotides or kits that are set forth herein may be used to detect, measure or identify a biological system (including, for example, processes or components thereof). Exemplary techniques that can employ the compounds, nucleotides or kits include sequencing, expression analysis, hybridisation analysis, genetic analysis, RNA analysis, cellular assay (e.g. cell binding or cell function analysis), or protein assay (e.g. protein binding assay or protein activity assay). The use may be on an automated instrument for carrying out a particular technique, such as an automated sequencing instrument. The sequencing instrument may contain two lasers operating at different wavelengths.

Disclosed herein is a method of synthesising compounds of the disclosure. A compound of formula (X) and/or (X1), (X2) or a salt thereof may be used as a starting material for the synthesis of symmetrical or unsymmetrical polymethine dyes:

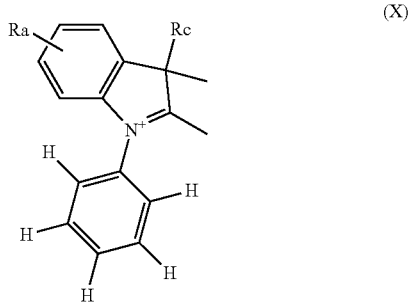
(X)

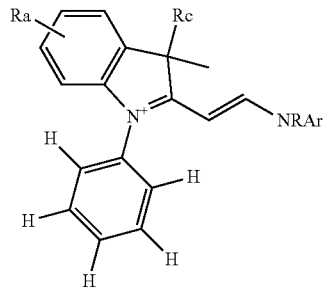
(X1)

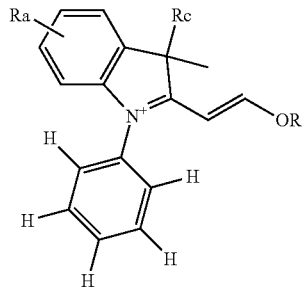
(X2)

wherein Ra is H, SO$_3^-$, sulphonamide, halogen, or a further ring fused to an adjacent carbon atoms;
Rb is optionally substituted aryl or optionally substituted alkyl; and
Rc is alkyl or substituted alkyl.

As used herein, the term "alkyl" refers to C1-C20 hydrocarbon and may include C3-C10 non-aromatic carbocyclic rings. In particular embodiments the alkyl groups are C1-C6 alkyl which refers to saturated, straight- or branched-chain hydrocarbon radicals containing between one and six carbon atoms, respectively. Alkyl groups may include one or more unsaturated groups, and thus include alkenyl and alkynyl.

The term "halogen" as used herein refers to fluoro- (hereafter designated as F), chloro- (hereafter designated as Cl), bromo- (hereafter designated as Br) or iodo- (hereafter designated as I), and usually relates to substitution for a hydrogen atom in an organic compound, this substitution is optionally a full substitution for the hydrogen.

The term "substituted alkyl", refers to alkyl, alkenyl or alkynyl groups as defined above where they may optionally be further substituted with, but not limited to, halo, cyano, SO$_3^-$, SRa, ORa, NRbRc, oxo, CONRbRc, COOH and COORb. Ra, Rb and Rc may be each independently selected from H, alkyl, substituted alkyl, alkenyl, substituted alkenyl, alkynyl, substituted alkynyl, aryl and substituted aryl. Further, said substituted alkyl, substituted alkenyl and substituted alkynyl may optionally be interrupted by at least one hetero atom or group selected from O, NRb, S(O)$_t$ where t is 0 to 2, and the like. Substituted alkyl also covers group such as benzyl where the alkyl groups is comprises a further aryl or substituted aryl moiety.

Dyes according to the present disclosure may be synthesised from a variety of different starting materials, including N-phenyl indoles. The dyes may be made symmetrically, such that the same indole is at both end of the trimethine chain, or unsymmetrically such that different indoles are at either end of the chromophore. Methods for preparing polymethine dyes are well known in the art.

According to an aspect of the disclosure there are provided dye compounds suitable for attachment to substrate moieties, particularly comprising linker groups to enable attachment to substrate moieties. Substrate moieties can be virtually any molecule or substance to which the dyes of the disclosure can be conjugated and, by way of non-limiting example, may include nucleosides, nucleotides, polynucleotides, carbohydrates, ligands, particles, solid surfaces, organic and inorganic polymers, chromosomes, nuclei, living cells and combinations or assemblages thereof. The dyes can be conjugated by an optional linker by a variety of means including hydrophobic attraction, ionic attraction and covalent attachment. Particularly the dyes are conjugated to the substrate by covalent attachment. More particularly the covalent attachment is by means of a linker group.

The dyes according to the present disclosure may include a reactive linker group at one of the substituent positions for covalent attachment of the dye to another molecule. Reactive linking groups are moieties capable of forming a bond (e.g. a covalent or non-covalent bond). In a particular embodiment the linker may be a cleavable linker. Use of the term "cleavable linker" is not meant to imply that the whole linker is required to be removed. The cleavage site can be located at a position on the linker that results in part of the linker remaining attached to the dye and/or substrate moiety after cleavage. Cleavable linkers may be, by way of non-limiting example, electrophilically cleavable linkers, enzymatically cleavable linkers, nucleophilically cleavable linkers, photocleavable linkers, cleavable under reductive conditions (for example disulfide or azide containing linkers), oxidative conditions, cleavable via use of safety-catch linkers and cleavable by elimination mechanisms. The use of a cleavable linker to attach the dye compound to a substrate moiety provides the option of removing the label, for example after detection, thereby avoiding any interfering signal in downstream steps.

Useful linker groups may be found in PCT publication number WO2004/018493 (herein incorporated by reference) examples of which include linkers that, may be cleaved using water-soluble phosphines or water-soluble transition metal catalysts formed from a transition metal and at least partially water-soluble ligands. In aqueous solution the latter form at least partially water-soluble transition metal complexes. Such cleavable linkers can be used to connect bases of nucleotides to labels such as the dyes set forth herein.

Particular linkers may be found in PCT publication number WO2004/018493 (herein incorporated by reference) such as those that include moieties of the formula:

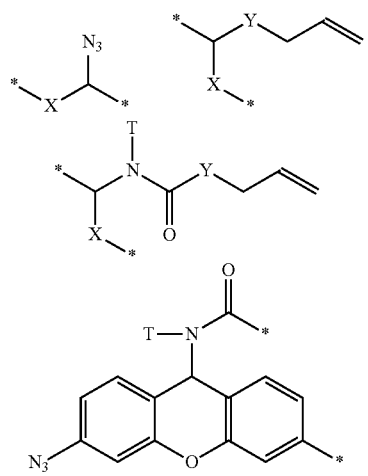

(wherein X is selected from the group comprising O, S, NH and NQ wherein Q is a C1-10 substituted or unsubstituted alkyl group, Y is selected from the group comprising O, S, NH and N(allyl), T is hydrogen or a C1-10 substituted or unsubstituted alkyl group and * indicates where the moiety is connected to the remainder of the nucleotide or nucleoside).

In particular embodiments, the length of the linker between a fluorescent dye (fluorophore) and a guanine base can be altered, for example, by introducing a polyethylene glycol spacer group, thereby increasing the fluorescence intensity compared to the same fluorophore attached to the guanine base through other linkages known in the art. Exemplary linkers and their properties are set forth in GB patent application number 0517097.2, published as WO07020457, (herein incorporated by reference). The design of linkers, and especially their increased length, can allow improvements in the brightness of fluorophores attached to the guanine bases of guanosine nucleotides when incorporated into polynucleotides such as DNA. Thus, when the dye is for use in any method of analysis which employs detection of a fluorescent dye label attached to a guanine-containing nucleotide, it can be advantageous to use a linker having a spacer group of formula $-((CH_2)_2O)_n-$ wherein n is an integer between 2 and 50, for example, as described in WO07020457.

The present disclosure further provides conjugates of nucleosides and nucleotides labelled with one or more of the dyes set forth herein (modified nucleotides). Labelled nucleosides and nucleotides are useful for labelling polynucleotides formed by enzymatic synthesis, such as, by way of non-limiting example, in PCR amplification, isothermal amplification, solid phase amplification, polynucleotide sequencing (e.g. solid phase sequencing), nick translation reactions and the like.

Nucleosides and nucleotides may be labelled at sites on the sugar or nucleobase. As known in the art, a "nucleotide" consists of a nitrogenous base, a sugar, and one or more phosphate groups. In RNA the sugar is ribose and in DNA is a deoxyribose, i.e. a sugar lacking a hydroxyl group that is present in ribose. The nitrogenous base is a derivative of purine or pyrimidine. The purines can be adenine (A) or guanine (G), and the pyrimidines can be cytosine (C), thymine (T) or in the context of RNA, uracil (U). The C-1 atom of deoxyribose is bonded to N-1 of a pyrimidine or N-9 of a purine. A nucleotide is also a phosphate ester of a nucleoside, with esterification occurring on the hydroxyl group attached to the C-3 or C-5 of the sugar. Nucleotides are usually mono, di- or triphosphates.

A "nucleoside" is structurally similar to a nucleotide but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of a parent compound but which has a chemical or physical modification, such as, for example, a different or additional side group, which allows the derivative nucleotide or nucleoside to be linked to another molecule. For example, the base may be a deazapurine. In particular embodiments, the derivatives are capable of undergoing Watson-Crick pairing. "Derivative" and "analogue" also include, for example, a synthetic nucleotide or nucleoside derivative having modified base moieties and/or modified sugar moieties. Such derivatives and analogues are discussed in, for example, Scheit, Nucleotide analogs (John Wiley & Son, 1980) and Uhlman et al., Chemical Reviews 90:543-584, 1990. Nucleotide analogues can also have modified phosphodiester linkages including phosphorothioate, phosphorodithioate, alkyl-phosphonate, phosphoranilidate, phosphoramidate linkages and the like.

A dye may be attached to any position on a nucleotide base, for example, through a linker. In particular embodiments Watson-Crick base pairing can still be carried out for the resulting analogue. Particular nucleobase labelling sites include the C5 position of a pyrimidine base or the C7 position of a 7-deaza purine base. As described above a linker group may be used to covalently attach a dye to the nucleoside or nucleotide.

In particular embodiments the labelled nucleoside or nucleotide may be enzymatically incorporable and enzymatically extendable. Accordingly a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit. The spacer distances, for example, the nucleotide base from a cleavage site or label.

Nucleosides or nucleotides labelled with dyes of the disclosure may have the formula:

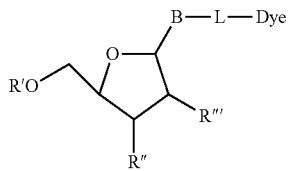

Where Dye is a dye compound according to the present disclosure, B is a nucleobase, such as, for example uracil, thymine, cytosine, adenine, guanine and the like and L is an optional linker group which may or may not be present. R' can be H, monophosphate, diphosphate, triphosphate, thiophosphate, a phosphate ester analog, —O— attached to a reactive phosphorous containing group or —O— protected by a blocking group. R" can be H, OH, a phosphoramidite or a 3'OH blocking group and R''' is H or OH.

Where R" is phosphoramidite, R' is an acid-cleavable hydroxyl protecting group which allows subsequent monomer coupling under automated synthesis conditions.

In a particular embodiment the blocking group is separate and independent of the dye compound, i.e. not directly attached to it. In an alternative embodiment the dye may comprise all or part of the 3'OH blocking group. Thus R" can be a 3'OH blocking group which may or may not comprise a dye compound disclosed herein.

In still yet another alternative embodiment there is no blocking group on the 3' carbon of the pentose sugar and the dye (or dye and linker construct) attached to the base, for example, can be of a size or structure sufficient to act as a block to the incorporation of a further nucleotide. Thus the block can be due to steric hindrance or can be due to a combination of size, charge and structure, whether or not the dye is attached to the 3' position of the sugar.

In still yet another alternative embodiment the blocking group is present on the 2' or 4' carbon of the pentose sugar and can be of a size or structure sufficient to act as a block to the incorporation of a further nucleotide.

The use of a blocking group allows polymerisation to be controlled, such as by stopping extension when a modified nucleotide is incorporated. If the blocking effect is reversible, for example by way of non-limiting example by changing chemical conditions or by removal of a chemical block, extension can be stopped at certain points and then allowed to continue.

In another particular embodiment a 3'OH blocking group will comprise moieties disclosed in WO2004/018497 (herein incorporated by reference). For example the blocking group may be azidomethyl ($CH_2N_3$) or allyl.

In a particular embodiment a linker (between dye and nucleotide) and a blocking group are both present and are separate moieties. In particular embodiments the linker and blocking group are both cleavable under substantially similar conditions. Thus deprotection and deblocking processes may be more efficient since only a single treatment will be required to remove both the dye compound and the block. However, in some embodiments a linker and blocking group need not be cleavable under similar conditions, instead being individually cleavable under distinct conditions.

This disclosure also encompasses polynucleotides incorporating dye compounds. Such polynucleotides may be DNA or RNA comprised respectively of deoxyribonucleotides or ribonucleotides joined in phosphodiester linkage. Polynucleotides according to the disclosure may comprise naturally occurring nucleotides, non-naturally occurring (or modified) nucleotides other than the modified nucleotides of the disclosure or any combination thereof, in combination with at least one modified nucleotide (e.g. labelled with a dye compound) set forth herein. Polynucleotides according to the disclosure may also include non-natural backbone linkages and/or non-nucleotide chemical modifications. Chimeric structures comprised of mixtures of ribonucleotides and deoxyribonucleotides comprising at least one modified nucleotide according to the disclosure are also contemplated.

Modified nucleotides (or nucleosides) comprising a dye compound according to the present disclosure may be used in any method of analysis such as methods that include detection of a fluorescent label attached to a nucleotide or nucleoside, whether on its own or incorporated into or associated with a larger molecular structure or conjugate. In this context the term "incorporated into a polynucleotide" can mean that the 5' phosphate is joined in phosphodiester linkage to the 3' hydroxyl group of a second (modified or unmodified) nucleotide, which may itself form part of a longer polynucleotide chain. The 3' end of a modified nucleotide set forth herein may or may not be joined in phosphodiester linkage to the 5' phosphate of a further (modified or unmodified) nucleotide. Thus, in one non-limiting embodiment the disclosure provides a method of detecting a modified nucleotide incorporated into a polynucleotide which comprises: (a) incorporating at least one modified nucleotide of the disclosure into a polynucleotide and (b) detecting the modified nucleotide(s) incorporated into the polynucleotide by detecting the fluorescent signal from the dye compound attached to said modified nucleotide(s).

This method can include: a synthetic step (a) in which one or more modified nucleotides according to the disclosure are incorporated into a polynucleotide and a detection step (b) in which one or more modified nucleotide(s) incorporated into the polynucleotide are detected by detecting or quantitatively measuring their fluorescence.

In one embodiment of the present disclosure at least one modified nucleotide is incorporated into a polynucleotide in a synthetic step by the action of a polymerase enzyme. However, other methods of joining modified nucleotides to polynucleotides, such as for example chemical oligonucleotide synthesis or ligation of labelled oligonucleotides to unlabelled oligonucleotides can be used. Therefore, the term "incorporating", when used in reference to a nucleotide and polynucleotide, can encompass polynucleotide synthesis by chemical methods as well as enzymatic methods.

In a specific embodiment a synthetic step is carried out and may optionally comprise incubating a template polynucleotide strand with a reaction mixture comprising fluorescently labelled modified nucleotides of the disclosure. A polymerase can also be provided under conditions which permit formation of a phosphodiester linkage between a free 3' hydroxyl group on a polynucleotide strand annealed to the template polynucleotide strand and a 5' phosphate group on the modified nucleotide. Thus, a synthetic step can include formation of a polynucleotide strand as directed by complementary base-pairing of nucleotides to a template strand.

In all embodiments of the method, the detection step may be carried out whilst the polynucleotide strand into which the modified nucleotides are incorporated is annealed to a template strand, or after a denaturation step in which the two strands are separated. Further steps, for example chemical or enzymatic reaction steps or purification steps, may be included between a synthetic step and a detection step. In particular, the target strand incorporating the modified nucleotide(s) may be isolated or purified and then processed further or used in a subsequent analysis. By way of example, target polynucleotides labelled with modified nucleotide(s) in a synthetic step may be subsequently used as labelled probes or primers. In other embodiments the product of a synthetic step set forth herein may be subject to further reaction steps and, if desired, the product of these subsequent steps can be purified or isolated.

Suitable conditions for a synthetic step will be well known to those familiar with standard molecular biology techniques. In one embodiment a synthetic step may be analogous to a standard primer extension reaction using nucleotide precursors, including modified nucleotides set forth herein, to form an extended target strand complementary to the template strand in the presence of a suitable polymerase enzyme. In other embodiments a synthetic step may itself form part of an amplification reaction producing a labelled double stranded amplification product comprised of annealed complementary strands derived from copying of target and template polynucleotide strands. Other exemplary synthetic steps include nick translation, strand displacement polymerisation, random primed DNA labelling etc. A particularly useful polymerase enzyme for a synthetic step is one that is capable of catalysing the incorporation of one or more of the modified nucleotides set forth herein. A variety of naturally occurring or modified polymerases can be used. By way of example, a thermostable polymerase can be used for a synthetic reaction that is carried out using thermocycling conditions, whereas a thermostable polymerase may not be desired for isothermal primer extension reactions. Suitable thermostable polymerases which are capable of incorporating the modified nucleotides according to the disclosure include those described in WO 2005/024010 or WO06120433, each of which is incorporated herein by reference. In synthetic reactions which are carried out at lower temperatures such as 37° C., polymerase enzymes need not necessarily be thermostable polymerases, therefore the choice of polymerase will depend on a number of factors such as reaction temperature, pH, strand-displacing activity and the like.

In specific non-limiting embodiments the disclosure encompasses methods of nucleic acid sequencing, re-sequencing, whole genome sequencing, single nucleotide polymorphism scoring, or any other application involving the detection of the modified nucleotide or nucleoside labelled with dyes set forth herein when incorporated into a polynucleotide. Any of a variety of other applications benefiting from the use of polynucleotides labelled with the modified nucleotides comprising fluorescent dyes can use modified nucleotides or nucleosides labelled with dyes set forth herein.

In a particular embodiment the disclosure provides use of modified nucleotides comprising dye compounds according to the disclosure in a polynucleotide sequencing-by-synthesis reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template nucleic acid to be sequenced. The identity of the base present in one or more of the added nucleotide(s) can be determined in a detection or "imaging" step. The identity of the added base may be determined after each nucleotide incorporation step. The sequence of the template may then be inferred using conventional Watson-Crick base-pairing rules. The use of the modified nucleotides labelled with dyes set forth herein for determination of the identity of a single base may be useful, for example, in the scoring of single nucleotide polymorphisms, and such single base extension reactions are within the scope of this disclosure.

In an embodiment of the present disclosure, the sequence of a template polynucleotide is determined by detecting the incorporation of one or more nucleotides into a nascent strand complementary to the template polynucleotide to be sequenced through the detection of fluorescent label(s) attached to the incorporated nucleotide(s). Sequencing of the template polynucleotide can be primed with a suitable primer (or prepared as a hairpin construct which will contain the primer as part of the hairpin), and the nascent chain is extended in a stepwise manner by addition of nucleotides to the 3' end of the primer in a polymerase-catalysed reaction.

In particular embodiments each of the different nucleotide triphosphates (A, T, G and C) may be labelled with a unique fluorophore and also comprises a blocking group at the 3' position to prevent uncontrolled polymerisation. Alternatively one of the four nucleotides may be unlabelled (dark). The polymerase enzyme incorporates a nucleotide into the nascent chain complementary to the template polynucleotide, and the blocking group prevents further incorporation of nucleotides. Any unincorporated nucleotides can be washed away and the fluorescent signal from each incorporated nucleotide can be "read" optically by suitable means, such as a charge-coupled device using laser excitation and suitable emission filters. The 3'-blocking group and fluorescent dye compounds can then be removed (deprotected), (simultaneously or sequentially) to expose the nascent chain for further nucleotide incorporation. Typically the identity of the incorporated nucleotide will be determined after each incorporation step but this is not strictly essential. Similarly, U.S. Pat. No. 5,302,509 (which is incorporated herein by reference) discloses a method to sequence polynucleotides immobilised on a solid support.

The method, as exemplified above, utilizes the incorporation of fluorescently labelled, 3'-blocked nucleotides A, G, C and T into a growing strand complementary to the immobilised polynucleotide, in the presence of DNA polymerase. The polymerase incorporates a base complementary to the target polynucleotide, but is prevented from further addition by the 3'-blocking group. The label of the incorporated nucleotide can then be determined and the blocking group removed by chemical cleavage to allow further polymerisation to occur. The nucleic acid template to be sequenced in a sequencing-by-synthesis reaction may be any polynucleotide that it is desired to sequence. The nucleic acid template for a sequencing reaction will typically comprise a double stranded region having a free 3' hydroxyl group which serves as a primer or initiation point for the addition of further nucleotides in the sequencing reaction. The region of the template to be sequenced will overhang this free 3' hydroxyl group on the complementary strand. The overhanging region of the template to be sequenced may be single stranded but can be double-stranded, provided that a "nick is present" on the strand complementary to the template strand to be sequenced to provide a free 3' OH group for initiation of the sequencing reaction. In such embodiments sequencing may proceed by strand displacement. In certain embodiments a primer bearing the free 3' hydroxyl group may be added as a separate component (e.g. a short oligonucleotide) which hybridises to a single-stranded region of the template to be sequenced. Alternatively, the primer and the template strand to be sequenced may each form part of a partially self-complementary nucleic acid strand capable of forming an intra-molecular duplex, such as for example a hairpin loop structure. Hairpin polynucleotides and methods by which they may be attached to solid supports are disclosed in International application publication nos. WO0157248 and WO2005/047301, each of which is incorporated herein by reference. Nucleotides can be added successively to a growing primer, resulting in synthesis of a polynucleotide chain in the 5' to 3' direction. The nature of the base which has been added may be determined, particularly but not necessarily after each nucleotide addition, thus providing sequence information for the nucleic acid template. Thus, a nucleotide is incorporated into a nucleic acid strand (or polynucleotide) by joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments the nucleic acid template to be sequenced may be attached to a solid support via any suitable linkage method known in the art, for example via covalent attachment. In certain embodiments template polynucleotides may be attached directly to a solid support (e.g. a silica-based support). However, in other embodiments of the disclosure the surface of the solid support may be modified in some way so as to allow either direct covalent attachment of template polynucleotides, or to immobilise the template polynucleotides through a hydrogel or polyelectrolyte multilayer, which may itself be non-covalently attached to the solid support.

Arrays in which polynucleotides have been directly attached to silica-based supports are those for example disclosed in WO00006770 (incorporated herein by reference), wherein polynucleotides are immobilised on a glass support by reaction between a pendant epoxide group on the glass with an internal amino group on the polynucleotide. In addition, polynucleotides can be attached to a solid support by reaction of a sulphur-based nucleophile with the solid support, for example, as described in WO2005/047301 (incorporated herein by reference). A still further example of solid-supported template polynucleotides is where the template polynucleotides are attached to hydrogel supported upon silica-based or other solid supports, for example, as described in WO00/31148, WO01/01143, WO02/12566, WO03/014392, U.S. Pat. No. 6,465,178 and WO00/53812, each of which is incorporated herein by reference.

A particular surface to which template polynucleotides may be immobilised is a polyacrylamide hydrogel. Polyacrylamide hydrogels are described in the references cited above and in WO2005/065814, which is incorporated herein by reference.

DNA template molecules can be attached to beads or microparticles, for example as described in U.S. Pat. No. 6,172,218 (which is incorporated herein by reference). Attachment to beads or microparticles can be useful for sequencing applications. Bead libraries can be prepared where each bead contains different DNA sequences. Exemplary libraries and methods for their creation are described in Nature. 437, 376-380 (2005); Science. 309, 5741, 1728-1732 (2005), each of which is incorporated herein by reference. Sequencing of arrays of such beads using nucleotides set forth herein is within the scope of the disclosure.

Template(s) that are to be sequenced may form part of an "array" on a solid support, in which case the array may take any convenient form. Thus, the method of the disclosure is applicable to all types of high density arrays, including single-molecule arrays, clustered arrays and bead arrays. Modified nucleotides labelled with dye compounds of the present disclosure may be used for sequencing templates on essentially any type of array, including but not limited to those formed by immobilisation of nucleic acid molecules on a solid support.

However, the modified nucleotides labelled with dye compounds of the disclosure are particularly advantageous in the context of sequencing of clustered arrays. In clustered arrays, distinct regions on the array (often referred to as sites, or features) comprise multiple polynucleotide template molecules. Generally, the multiple polynucleotide molecules are not individually resolvable by optical means and are instead detected as an ensemble. Depending on how the array is formed, each site on the array may comprise multiple copies of one individual polynucleotide molecule (e.g. the site is homogenous for a particular single- or double-stranded nucleic acid species) or even multiple copies of a small number of different polynucleotide molecules (e.g. multiple copies of two different nucleic acid species). Clustered arrays of nucleic acid molecules may be produced using techniques generally known in the art. By way of example, WO 98/44151 and WO00/18957, each of which is incorporated herein, describe methods of amplification of nucleic acids wherein both the template and amplification products remain immobilised on a solid support in order to form arrays comprised of clusters or "colonies" of immobilised nucleic acid molecules. The nucleic acid molecules present on the clustered arrays prepared according to these methods are suitable templates for sequencing using the modified nucleotides labelled with dye compounds of the disclosure.

The modified nucleotides labelled with dye compounds of the present disclosure are also useful in sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to individually resolve the individual polynucleotide molecules. The target nucleic acid molecules immobilised onto the surface of the solid support can thus be capable of being resolved by optical means in some embodiments. This means that one or more distinct signals, each representing one polynucleotide, will occur within the resolvable area of the particular imaging device used.

Single molecule detection may be achieved wherein the spacing between adjacent polynucleotide molecules on an array is at least 100 nm, more particularly at least 250 nm, still more particularly at least 300 nm, even more particularly at least 350 nm. Thus, each molecule is individually resolvable and detectable as a single molecule fluorescent point, and fluorescence from said single molecule fluorescent point also exhibits single step photobleaching.

The terms "individually resolved" and "individual resolution" are used herein to specify that, when visualised, it is possible to distinguish one molecule on the array from its neighbouring molecules. Separation between individual molecules on the array will be determined, in part, by the particular technique used to resolve the individual molecules. The general features of single molecule arrays will be understood by reference to published applications WO00/06770 and WO 01/57248, each of which is incorporated herein by reference. Although one use of the modified nucleotides of the disclosure is in sequencing-by-synthesis reactions, the utility of the modified nucleotides is not limited to such methods. In fact, the nucleotides may be used advantageously in any sequencing methodology which requires detection of fluorescent labels attached to nucleotides incorporated into a polynucleotide.

In particular, the modified nucleotides labelled with dye compounds of the disclosure may be used in automated fluorescent sequencing protocols, particularly fluorescent dye-terminator cycle sequencing based on the chain termination sequencing method of Sanger and co-workers. Such methods generally use enzymes and cycle sequencing to incorporate fluorescently labelled dideoxynucleotides in a primer extension sequencing reaction. So called Sanger sequencing methods, and related protocols (Sanger-type), utilize randomised chain termination with labelled dideoxynucleotides.

Thus, the present disclosure also encompasses modified nucleotides labelled with dye compounds which are dideoxynucleotides lacking hydroxyl groups at both of the 3' and 2' positions, such modified dideoxynucleotides being suitable for use in Sanger type sequencing methods and the like.

Modified nucleotides labelled with dye compounds of the present disclosure incorporating 3' blocking groups, it will be recognized, may also be of utility in Sanger methods and related protocols since the same effect achieved by using modified dideoxy nucleotides may be achieved by using modified nucleotides having 3'-OH blocking groups: both prevent incorporation of subsequent nucleotides. Where nucleotides according to the present disclosure, and having a 3' blocking group are to be used in Sanger-type sequencing methods it will be appreciated that the dye compounds or detectable labels attached to the nucleotides need not be connected via cleavable linkers, since in each instance where a labelled nucleotide of the disclosure is incorporated; no nucleotides need to be subsequently incorporated and thus the label need not be removed from the nucleotide.

The present disclosure also provides kits including modified nucleosides and/or nucleotides labelled with dyes. Such kits will generally include at least one modified nucleotide or nucleoside labelled with a dye set forth herein together with at least one further component. The further component(s) may be one or more of the components identified in a method set forth above or in the Examples section below. Some non-limiting examples of components that can be combined into a kit of the present disclosure are set forth below.

In a particular embodiment, a kit can include at least one modified nucleotide or nucleoside labelled with a dye set forth herein together with modified or unmodified nucleotides or nucleosides. For example, modified nucleotides labelled with dyes according to the disclosure may be supplied in combination with unlabelled or native nucleotides, and/or with fluorescently labelled nucleotides or any combination thereof. Accordingly the kits may comprise modified nucleotides labelled with dyes according to the disclosure and modified nucleotides labelled with other, for example, prior art dye compounds. Combinations of nucleotides may be provided as separate individual components (e.g. one nucleotide type per vessel or tube) or as nucleotide mixtures (e.g. two or more nucleotides mixed in the same vessel or tube).

Where kits comprise a plurality, particularly two, more particularly four, modified nucleotides labelled with a dye compound, the different nucleotides may be labelled with different dye compounds, or one may be dark, with no dye compounds. Where the different nucleotides are labelled with different dye compounds it is a feature of the kits that said dye compounds are spectrally distinguishable fluorescent dyes. As used herein, the term "spectrally distinguishable fluorescent dyes" refers to fluorescent dyes that emit fluorescent energy at wavelengths that can be distinguished by fluorescent detection equipment (for example, a commercial capillary based DNA sequencing platform) when two or more such dyes are present in one sample. When two modified nucleotides labelled with fluorescent dye compounds are supplied in kit form, it is a feature of some embodiments that the spectrally distinguishable fluorescent dyes can be excited at the same wavelength, such as, for example by the same laser. When four modified nucleotides labelled with fluorescent dye compounds are supplied in kit form, it is a feature of some embodiments that two of the spectrally distinguishable fluorescent dyes can both be excited at one wavelength and the other two spectrally distinguishable dyes can both be excited at another wavelength. Particular excitation wavelengths are 532 nm, 630 nm to 700 nm, particularly 660 nm.

In one embodiment a kit includes a modified nucleotide labelled with a compound of the present disclosure and a second modified nucleotide labelled with a second dye wherein the dyes have a difference in absorbance maximum of at least 10 nm, particularly 20 nm to 50 nm. More particularly the two dye compounds have Stokes shifts of between 15-40 nm where "Stokes shift" is the distance between the peak absorption and peak emission wavelengths.

In a further embodiment a kit can further include two other modified nucleotides labelled with fluorescent dyes wherein the dyes are excited by the same laser at 600 nm to 700 nm, particularly 630 nm to 700 nm, more particularly 660 nm. The dyes can have a difference in absorbance maximum of at least 10 nm, particularly 20 nm to 50 nm. More particularly the two dye compounds can have Stokes shifts of between 20-40 nm. Still yet more particularly the two dye compounds can have a different absorbance maximum above 600 nm, particularly above 640 nm. Particular dyes which are spectrally distinguishable from polymethine dyes of the present disclosure and which meet the above criteria are polymethine analogues as described in U.S. Pat. No. 5,268,486 (for example Cy5) or WO 0226891 (Alexa 647; Molecular Probes A20106) or unsymmetrical polymethines as disclosed in U.S. Pat. No. 6,924,372, each of which is incorporated herein by reference.

In an alternative embodiment, the kits of the disclosure may contain nucleotides where the same base is labelled with two different compounds. A first nucleotide may be labelled with a compound of the disclosure. A second nucleotide may be labelled with a spectrally distinct compound, for example a 'red' dye absorbing at greater than 600 nm. A third nucleotide may be labelled as a mixture of the compound of the disclosure and the spectrally distinct compound, and the fourth nucleotide may be 'dark' and contain no label. In simple terms therefore the nucleotides 1-4 may be labelled 'green', 'red', 'red/green', and dark. To simplify the instrumentation further, four nucleotides can be labelled with a two dyes excited with a single laser, and thus the labelling of nucleotides 1-4 may be 'green 1', 'green 2' 'green 1/green 2', and dark.

Nucleotides may contain two dyes of the present disclosure. Dyes where $R_1$ and $R_4$ are H absorb at a lower wavelength than where $R_1$ and $R_4$ are alkyl. A kit may contain two or more nucleotides labelled with dyes of the disclosure. A kit may contain a nucleotide labelled with a compound of the disclosure where $R_1$ and $R_4$ are H, and a second nucleotide labelled with a compound of the disclosure where $R_1$ and $R_4$ are alkyl. Kits may contain a further nucleotide where a portion of the nucleotide is labelled with a compound of the disclosure where $R_1$ and $R_4$ are H, and a second portion of the nucleotide labelled with a compound of the disclosure where $R_1$ and $R_4$ are alkyl. Kits may further contain an unlabelled nucleotide.

Although kits are exemplified above in regard to configurations having different nucleotides that are labelled with different dye compounds, it will be understood that kits can include 2, 3, 4 or more different nucleotides that have the same dye compound.

In particular embodiments a kit may include a polymerase enzyme capable of catalyzing incorporation of the modified nucleotides into a polynucleotide. Other components to be included in such kits may include buffers and the like. The modified nucleotides labelled with dyes according to the disclosure, and other any nucleotide components including mixtures of different nucleotides, may be provided in the kit in a concentrated form to be diluted prior to use. In such embodiments a suitable dilution buffer may also be included. Again, one or more of the components identified in a method set forth herein can be included in a kit of the present disclosure.

It is noted that, as used in this specification and the appended claims, the singular forms "a", "an" and "the" include plural referents unless expressly and unequivocally limited to one referent. It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

Experimental Details 2,3,3-Trimethyl-1-phenyl-3H-indolium-5-sulfonate (1)

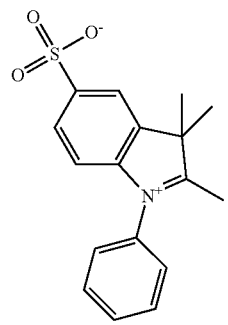

Molecular Weight = 315.39
Molecular Formula = C17H17NO3S

2-Methylene-3,3-trimethyl-1-phenyl-2,3-dihydro-1H-indole (1 g, 4.25 mmol) was dissolved in 1 ml of sulphuric acid at temperature <5° C. and 1 ml fuming sulphuric acid (20%) was added with stirring. The solution was stirred at room temperature 1 h then heated at 60° C. for 3 h. Product precipitated with diethyl ether washed with acetone and ethanol. Yield 0.7 g (52%). The structure was confirmed by NMR.

2-(2-Anilinovinyl-1)-3,3-trimethyl-1-phenyl-3H-indolium-5-sulfonate (2-1)

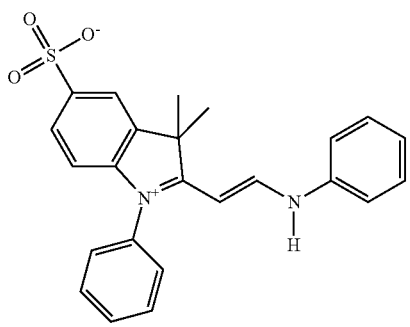 [SMILES: CC1(C)C(/C=C/Nc2ccccc2)=[N+](c2ccccc2)c2ccc(S(=O)(=O)[O-])cc21]

Reaction Scheme:

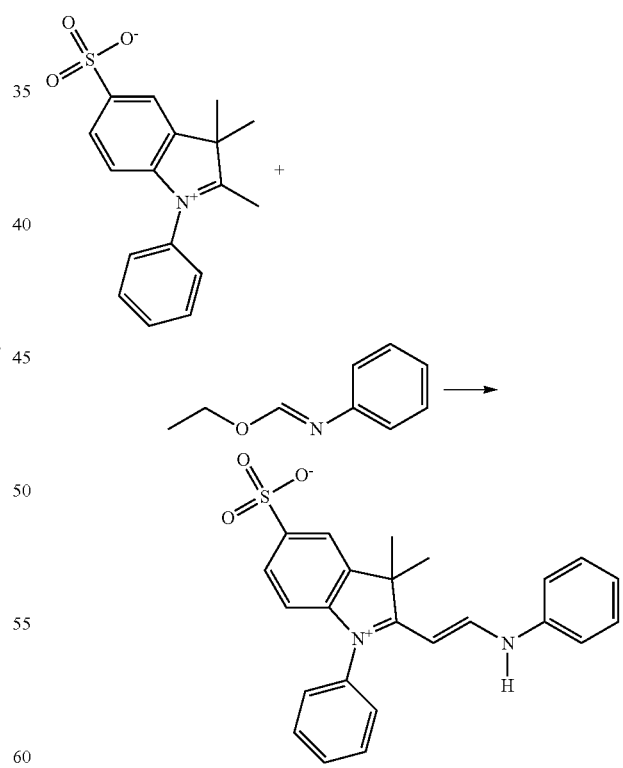

A mixture of 2,3,3-trimethyl-1-phenyl-3H-indolium-5-sulfonate (0.63 g) and ethyl N-phenylformimidate (0.5 g) was heated at 70° C. for 30 min. An orange melt formed. The product triturated with diethyl ether and filtered off. Yield 0.7 g (84%).

21

2-(2-Acetanilidovinyl-1)-3,3-trimethyl-1-phenyl-3H-indolium-5-sulfonate (2-2)

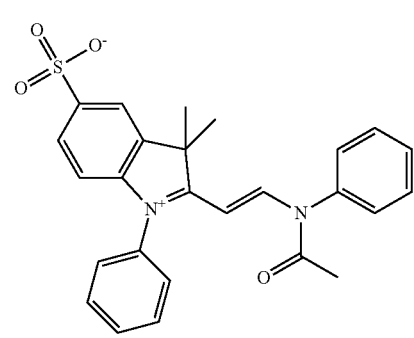 [SMILES: CC(=O)N(/C=C/C1=[N+](c2ccccc2)c2ccc(S(=O)(=O)[O-])cc2C1(C)C)c1ccccc1]

Reaction Scheme:

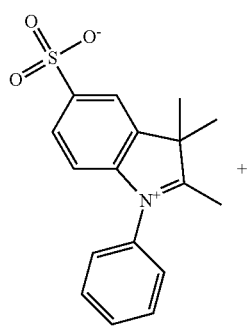

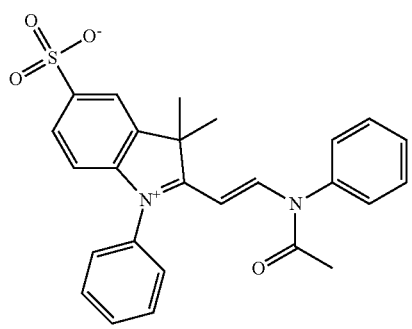

A mixture of 2,3,3-trimethyl-1-phenyl-3H-indolium-5-sulfonate (0.63 g), N,N'-diphenylformimidine (0.5 g), acetic acid (1 ml) and acetic anhydride (2 ml) was heated at 70° C. for 3 hours and then at 50° C. overnight. A yellow solution formed. The product was filtered off and washed with diethyl ether. Yield 0.69 g (75%).

22

1,2-dimethyl-1-(4-sulfonatobutyl)-3-phenyl-1H-benzo[e]indolium (3)

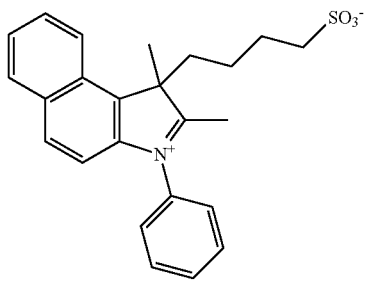

Reaction Scheme:

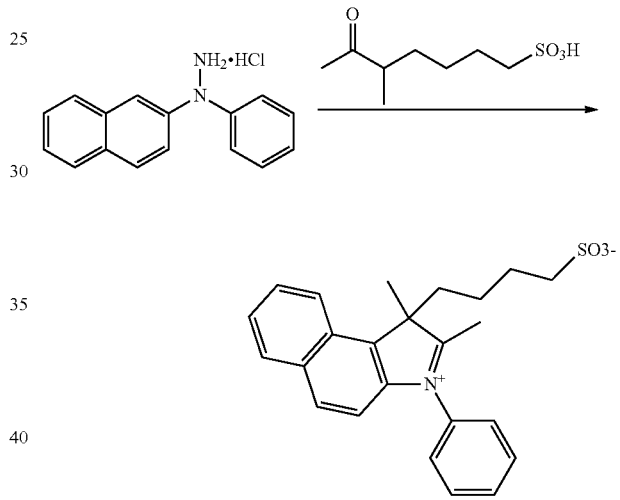

N-(2-Naphtyl), N-phenylhydrazine hydrochloride (19.51 mmol, 5.28 g), 5-methyl-6-oxoheptanesulfonic acid (17.18 mmol, 3.70 g) and anhydrous $ZnCl_2$ (17.18 mmol, 2.34 g) in absolute ethanol (30 ml) were stirred at room temperature for 30 min, then at 80° C. for 2 h. the reaction progress was checked by TLC (10% $H_2O$ in $CH_3CN$). After completion the reaction was cooled down and the solvent removed under vacuum. The residue was dissolved in DCM and purified by flash column on silica-gel. Yield: 3.06 g, 42%.

Proton NMR: (MeOH-D4): 8.28 (0.5H, d, J=8 Hz); 8.05-8.02 (1H, m); 7.89 (0.5H, d, J=8 Hz); 7.75-7.66 (3H, m); 7.65-7.60 (1H, m); 1.49-1.43 (1.5H, m); 7.31-7.25 (2H, m); 7.16 (0.5H, d, J=9 Hz); 7.07 (0.5H, appt, J=7.4 Hz); 6.61 (0.5H, d, J=8 Hz); 2.85-2.35 (4H, m); 1.88 (3H, appd, J=9 Hz); 1.75-1.4 (5H, m); 1.35-1.25 (0.5H, m); 1.1-0.95 (0.5H, m); 0.8-0.65 (0.5H, m); 0.58-0.45 (0.5H, m).

1,2-Dimethyl-1-(3-sulfonatopropyl)-3-phenyl-1H-benzo[e]indolium (4)

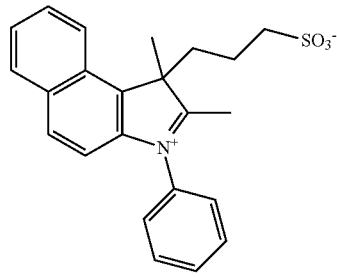

Reaction Scheme:

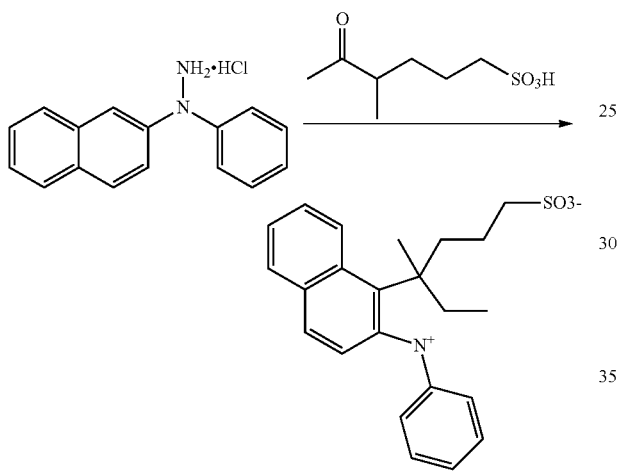

The title compound was prepared as the previous compound from N-(2-naphtyl)-N-phenylhydrazine hydrochloride and 4-methyl-5-oxopentanesulfonic acid. The product was purified by flash column on silicagel. Yield: 40%. Structure confirmed by NMR spectrum.

2,3-Dimethyl-3-(4-sulfonatobutyl)-1-phenyl-3H-indolium (5)

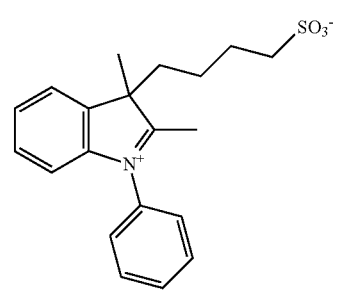

Reaction Scheme:

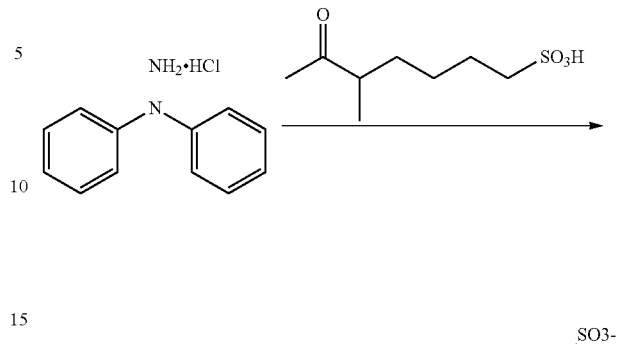

N,N-Diphenylhydrazine hydrochloride (0.01 mol, 2.2 g), 5-methyl-6-oxoheptanesulfonic acid (0.017 mol, 3.0 g) in glacial acetic acid (20 ml) were stirred at room temperature (~20° C.) for an hour then at 100° C. for 3 hours (TLC check). The reaction mixture was cooled down and the solvent removed under vacuum. The residue was washed with diethyl ether and purified by flash column on silicagel. Yield: 2 g (56%). Structure confirmed by NMR spectrum.

Indocarbocyanine I-2 (6)

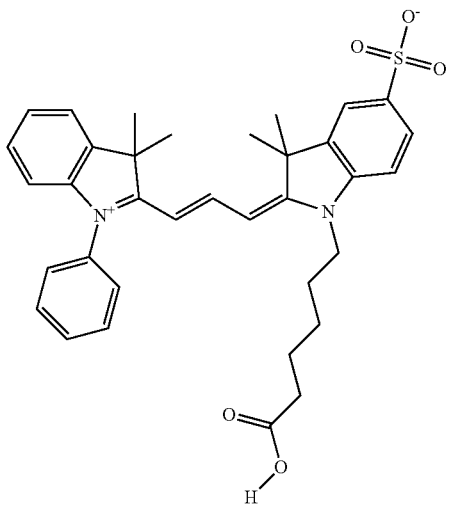 [SMILES: CC1(C)C(/C=C/C=C2/N(CCCCCC(=O)O)c3ccc(S(=O)(=O)[O-])cc3C2(C)C)=[N+](c2ccccc2)c2ccccc21]

25

Chemical Name

2-{(5-[1-phenyl-3,3-dimethyl)-1,2-dihydro-3H-indol-2-ylidene]-1-propen-1-yl}-3,3-dimethyl-1-(5-carboxypenthyl)-indolium-5-sulfonate Reaction Scheme:

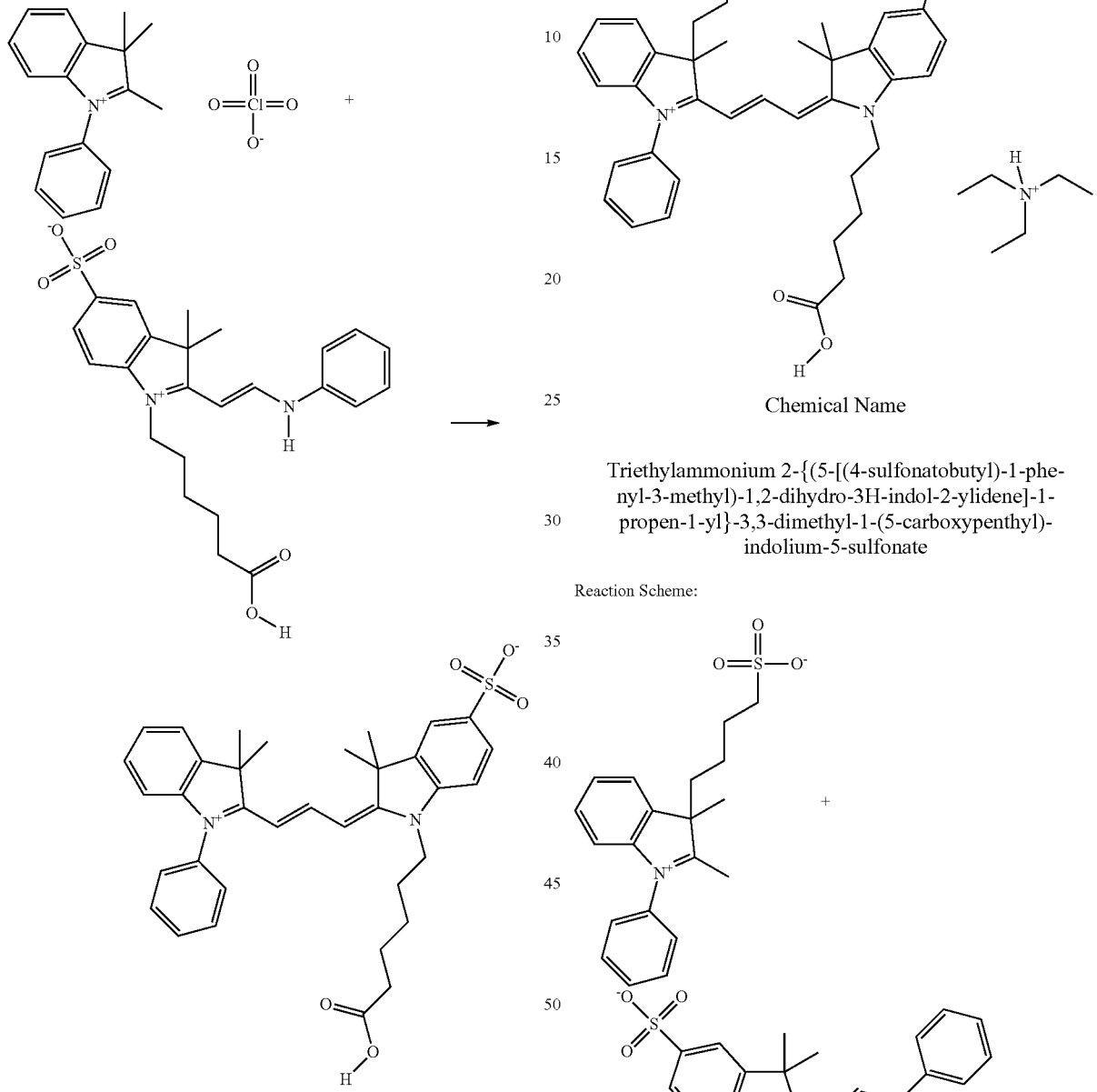

3,3-Dimethyl-1-(5-carboxypenthyl-2-(4-anilinovinyl)-3H-indolium-5-sulfonate (0.46 g) and 2,3,3-Trimethyl-1-phenyl-3H-indolium perchlorate (0.34 g) in mixture of acetic anhydride (2 ml) and acetic acid (1 ml) were stirred at room temperature (~25° C.) for 0.5 hour. Then to this solution pyridine (0.5 ml) was added. The reaction mixture was stirred at 80° C. for 3 h. Completion of the reaction was checked by TLC (20% H₂O in CH₃CN) and by UV measurement. Once the reaction finished, the red coloured mixture was cooled down and the solvents were removed under vacuum. The residue was purified by C18 flash column (TEAB 0.1 M in water and acetonitrile). Yield: 0.33 g (55%).

26

Indocarbocyanine I-4 (7)

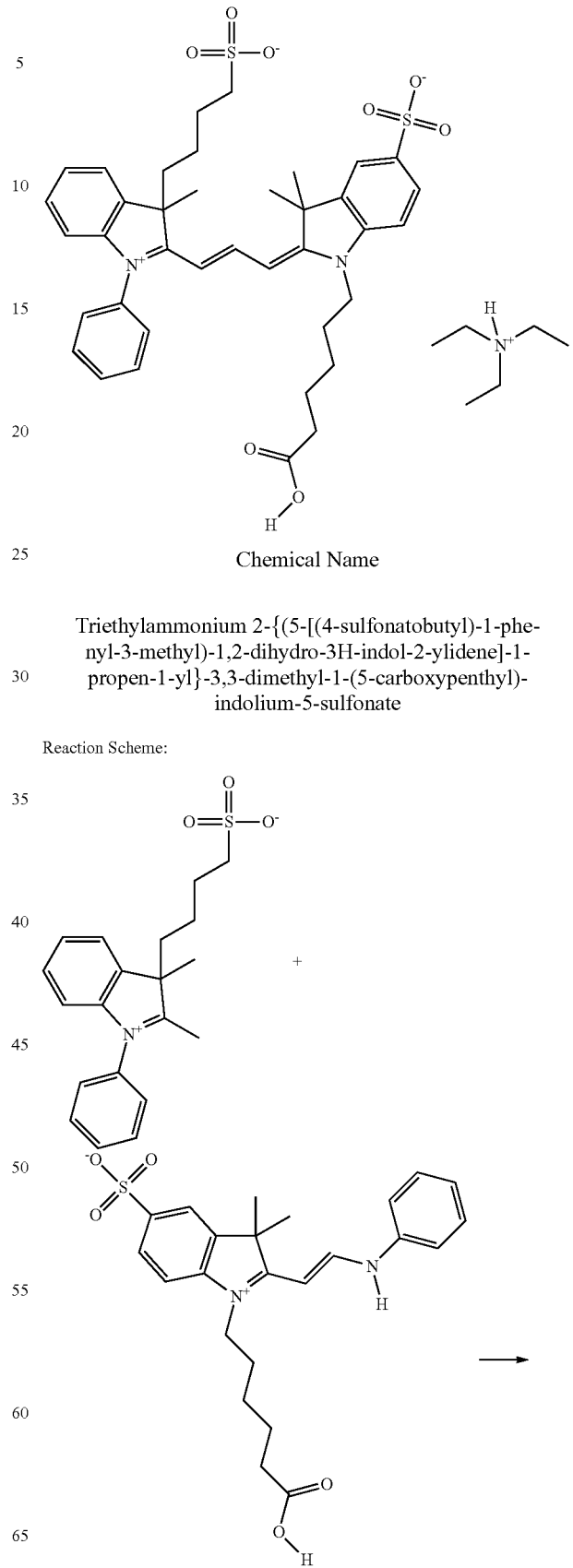

Chemical Name

Triethylammonium 2-{(5-[(4-sulfonatobutyl)-1-phenyl-3-methyl)-1,2-dihydro-3H-indol-2-ylidene]-1-propen-1-yl}-3,3-dimethyl-1-(5-carboxypenthyl)-indolium-5-sulfonate Reaction Scheme:

-continued

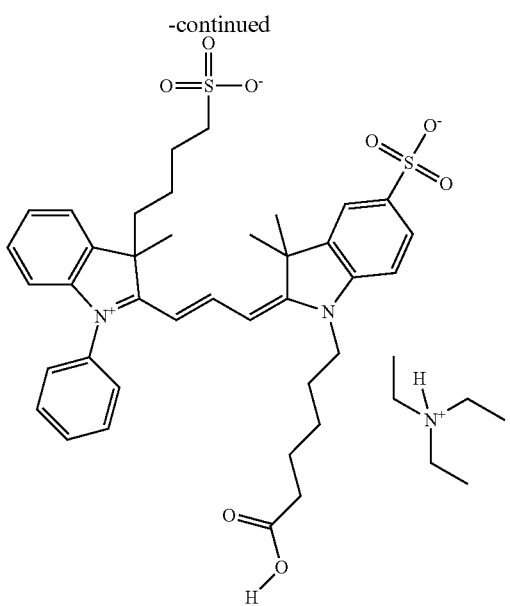

3,3-Dimethyl-1-(5-carboxypenthyl-2-(4-anilinovinyl)-3H-indolium-5-sulfonate (0.46 g) and 2,3-dimethyl-3-(4-sulfonatobutyl)-1-phenyl-3H-indolium (0.36 g) in mixture of acetic anhydride (2 ml) and acetic acid (1 ml) were stirred at room temperature (~25° C.) for 0.5 hour. Then to this solution pyridine (1 ml) was added. The reaction mixture was stirred at 80° C. for 3 h/completion of the reaction checked by TLC (20% $H_2O$ in $CH_3CN$)/and by UV measurement). Once the reaction finished, the red coloured reaction mixture was cooled down and most of the solvents were removed under vacuum. The residue was purified by C18 flash column (TEAB 0.1 M in water and acetonitrile). Yield: 0.29 g (35%).

Indocarbocyanine I-5 (8)

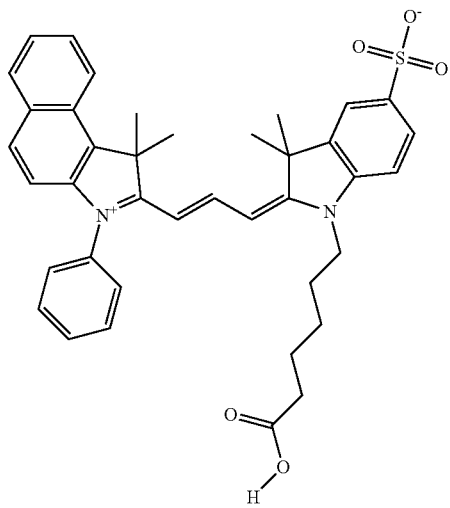 [SMILES: CC1(C)C(/C=C/C=C2/N(CCCCCC(=O)O)c3ccc(S(=O)(=O)[O-])cc3C2(C)C)=[N+](c2ccccc2)c2ccc3ccccc3c21]

Chemical Name

2-{(5-[(3-phenyl-1,1-dimethyl)-2,3-dihydro-1H-benzo[e]indol-2-ylidene]-1-propen-1-yl}-3,3-dimethyl-1-(5-carboxypenthyl)-indolium-5-sulfonate Reaction Scheme:

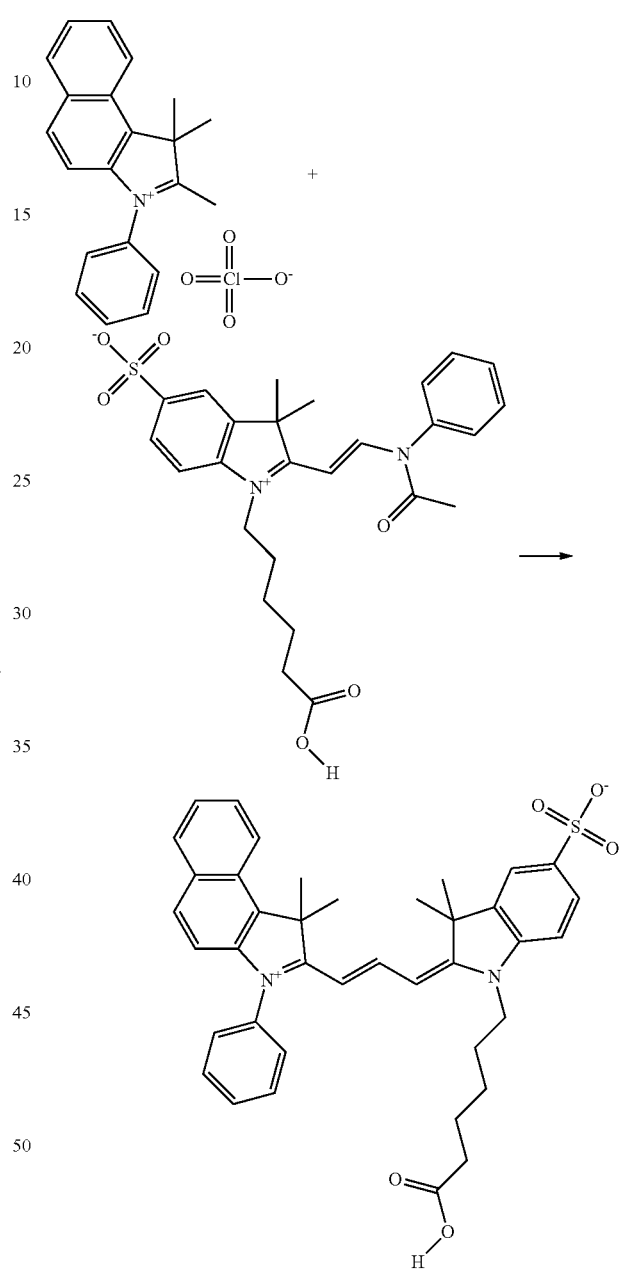

3,3-Dimethyl-1-(5-carboxypenthyl-2-(4-anilidovinyl)-3H-indolium-5-sulfonate (0.46 g) and 1,1,2-trimethyl-3-phenyl-3H-indolium perchlorate (0.39 g) in mixture of acetic anhydride (1 ml) and acetic acid (1 ml) were stirred at room temperature (~25° C.) for 0.5 hour. Then to this solution pyridine (1 ml) was added. The reaction mixture was stirred at 60° C. for 3 h/the reaction progress checked by TLC (20% $H_2O$ in $CH_3CN$)/and by UV measurement. Once the reaction finished, the red coloured reaction mixture was cooled down and most of the solvents were removed under vacuum. The residue was purified by C18 flash column (TEAB 0.1 M in water and acetonitrile). Yield: 0.38 g (54%).

Dye Conjugate (I-5-1) pppT-I-2

Reaction Scheme:

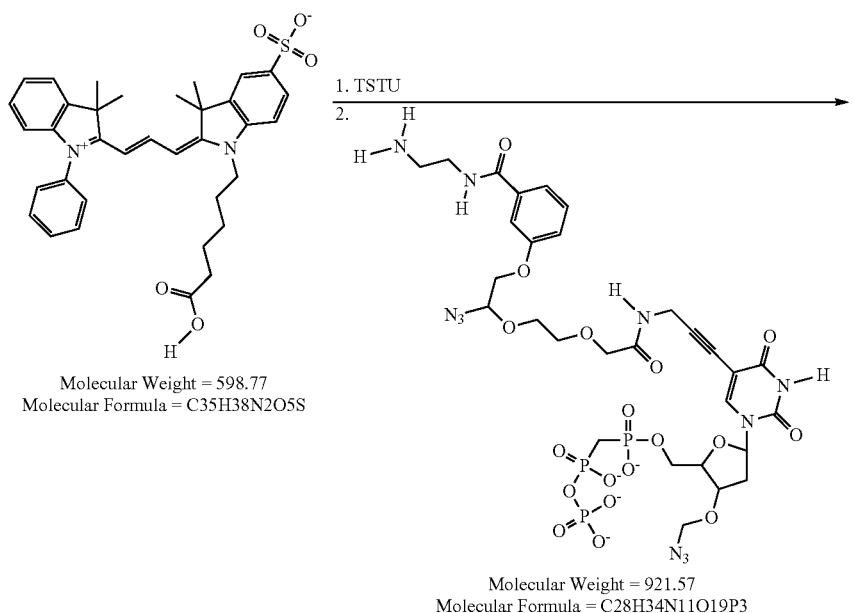

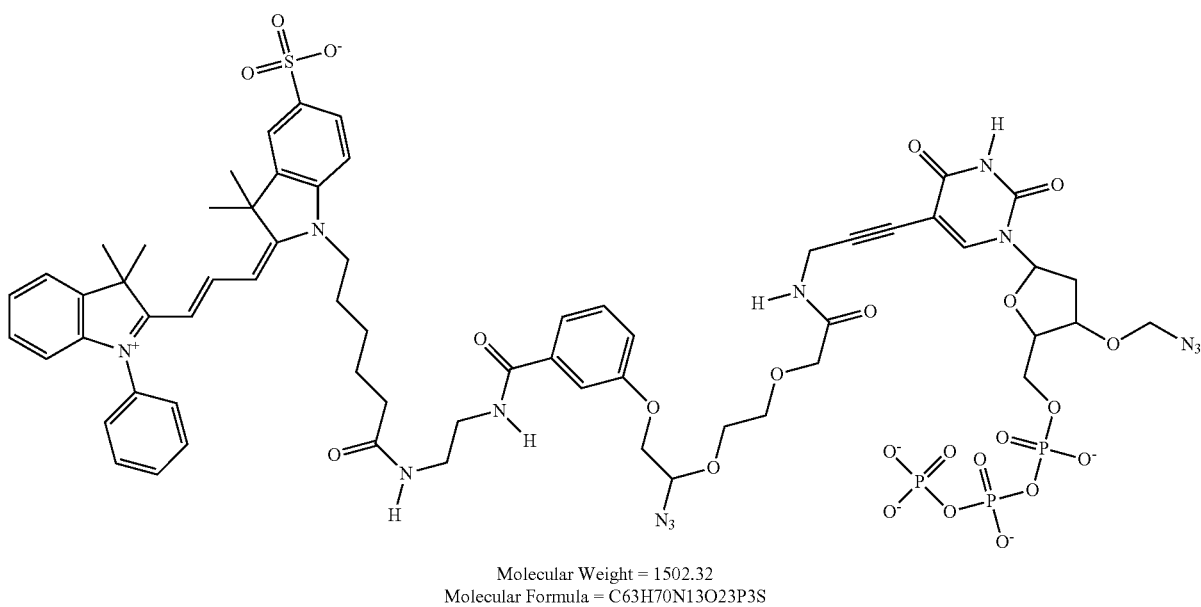

Preparation:

Anhydrous DMA (5 mL) and Hunig's Base (0.06 mL) were added to the dried sample of the dye (I-2) (60 mg). A solution of TSTU, (0.25 g) in 5 mL of dry DMA was then added to this. The red colour of activated ester developed. The reaction mixture was stirred at room temperature for 1 h. According to TLC (20% $H_2O$ in $CH_3CN$) the activation was completed. After activation was completed this solution was added to the solution of pppT-LN3 (0.23 g) in water (7 mL). The reaction mixture was stirred at room temperature under nitrogen atmosphere for 3 h. The coupling progress was checked by TLC (20% $H_2O$ in acetonitrile). The reaction mixture was cooled down to ~4° C. with an ice-bath, then a solution of 0.1 M TEAB (5 mL) in water was added and the mixture was stirred at room temperature for 10 min. The reaction mixture was applied to column with ~50 g of DEAE sephadex resin suspension in 0.05 M TEAB solution in water and washed with TEAB (concentration gradient from 0.1 M up to 0.5 M). Coloured fractions were collected and evaporated then co-evaporated again with water to remove more TEAB and vac down to dryness. The residue was then re-dissolved in TEAB 0.1 M. This solution was filtered through a syringe filter 0.2 nm pore size into a corning flask and stored in the freezer. The product was purified by HPLC using C18 reverse phase column with acetonitrile-0.1 M TEAB. Yield 67%.

Dye Conjugate (I-5-2) pppT-I-4

Reaction Scheme:

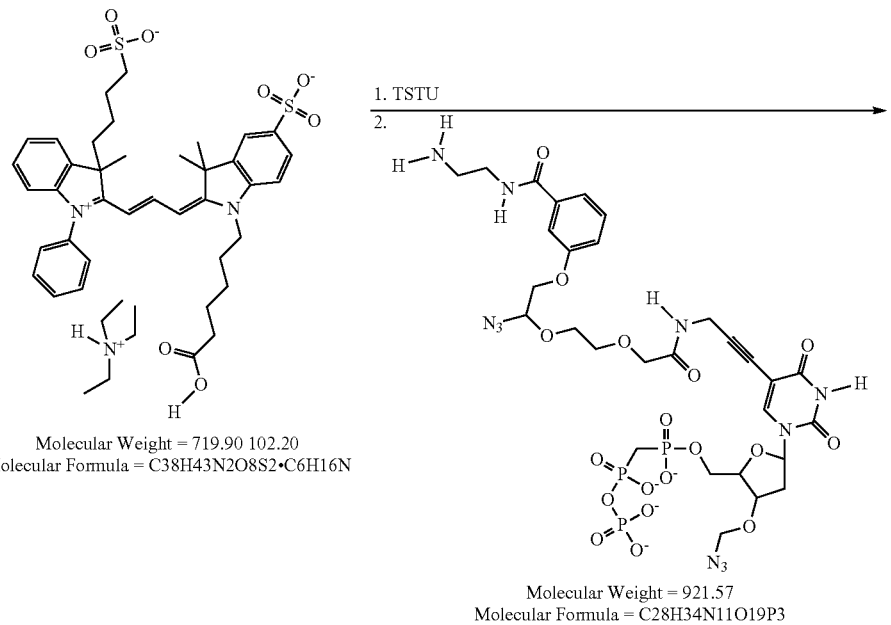

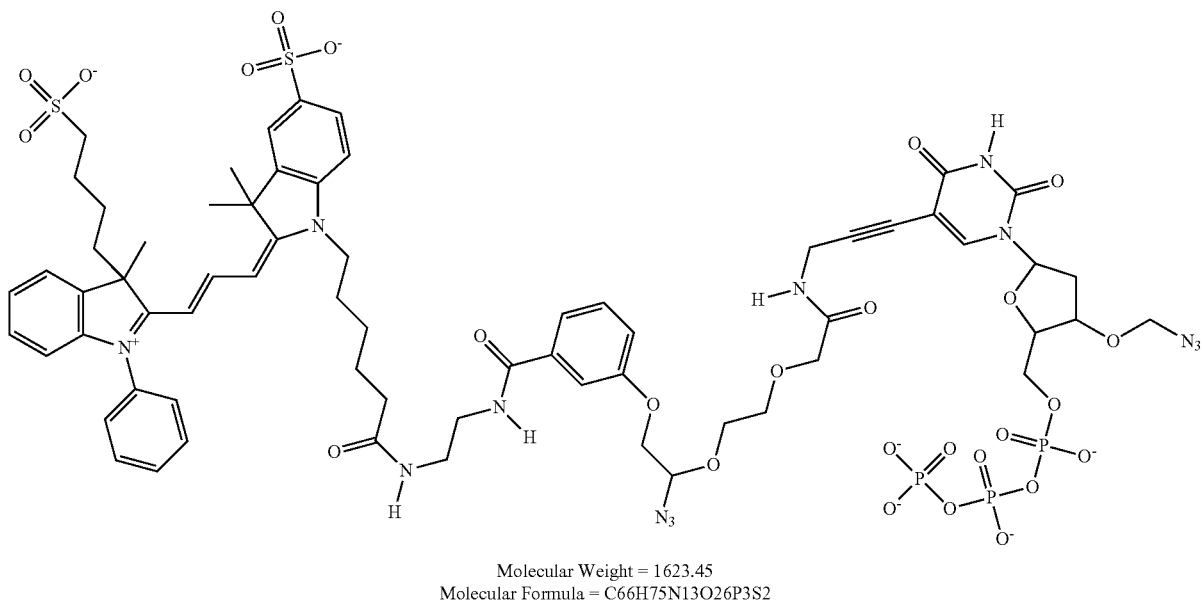

Preparation:

Anhydrous DMA (5 mL) and Hunig's Base (0.06 mL) were added to the dried sample of the dye (I-2) (82 mg). A solution of TSTU, (0.25 g) in 5 mL of dry DMA was then added to this. The red colour of activated ester developed soon. The reaction mixture was stirred at room temperature for 1 h. After activation was completed (TLC: 15% $H_2O$ in $CH_3CN$) this solution was added to the solution of pppT-LN3 (0.23 g) in water (7 mL). The reaction mixture was stirred at room temperature under nitrogen atmosphere for 3 h. The reaction mixture was cooled down to ~4° C. with an ice-bath, then a solution of 0.1 M TEAB (5 mL) in water was added and the mixture was stirred at room temperature for 10 min. The reaction mixture was applied to column with ~75 g of DEAE Sephadex resin suspension in 0.05 M TEAB solution in water and washed with TEAB (concentration gradient from 0.10 M up to 0.75 M). Red coloured fractions were collected, the solvent evaporated and then the residue co-evaporated again with water to remove more TEAB and vac down to dryness. The dye was then re-dissolved in TEAB 0.1 M. This solution was filtered through a syringe filter 0.2 nm pore size and the product was purified by HPLC using C18 reverse phase column with acetonitrile-0.1 M TEAB. Yield 70%.

TABLE 1

|  | Dye | Kd uM | Vmax s−1 | efficiency uM⁻¹s⁻¹ |
|---|---|---|---|---|
| pppT | DEG527 | 4.29 | 1.67 | 0.4 |
| pppT | Dy681 | 0.39 | 0.88 | 2.3 |
| pppT | I-2 | 0.33 | 1.51 | 4.5 |

Table 1 demonstrates that the incorporation ratio of the 3'-azidomethylthymidine triphosphate labelled with the dye I-2 is more than 10 times faster when compared with 3'-azidomethylthymidine triphosphate analogues labelled with alternative dyes.

TABLE 2

|  | Pol 217 Kd uM | Pol 957 EA Kd uM |
|---|---|---|
| ffT-Deg527 | 3.00 | 1.80 |
| Dark ffT | — | 0.55 |
| ffT-I-2 | 0.25 | 0.14 |

Table 2 demonstrates that the binding affinity of 3'-azidomethylthymidine triphosphate labelled with the dye I-2 is more than 10 times more efficient when compared with 3'-azidomethylthymidine triphosphate analogues labelled with alternative dyes and is also more efficient than unlabelled 3'-azidomethylthymidine triphosphate.

The dyes as shown by example I-2 are particularly advantageous for the efficient incorporations of their labelled nucleotide analogues. This is due to their much higher binding affinity (lower Kd) to the polymerase. The nucleotides with higher binding affinity can be used with the same incorporation efficiency as nucleotides with lower affinities, but at a much lower concentration. The amount of nucleotide required per cycle of sequencing reagent is therefore reduced without lower the quality of the sequencing data obtained.

The invention claimed is:

1. A compound of formula (I) or mesomeric forms thereof:

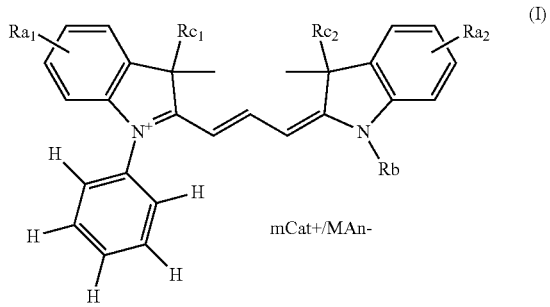

(I)

wherein mCat+ or mAn− is an organic or inorganic positively/negatively charged counterion and m is an integer 0-3;
each of $Ra_1$ and $Ra_2$ is independently H, $SO_3^-$, sulfonamide, halogen, or a further ring fused to an adjacent carbon atom;
Rb is optionally substituted aryl or optionally substituted alkyl;
each of $Rc_1$ and $Rc_2$ is independently alkyl or substituted alkyl; and
either Rb or one of $Rc_1$ or $Rc_2$ contains a linking moiety for further attachment or is linked to a further molecule;

wherein one of the Ra groups is a further fused ring forming a structure of formula (II):

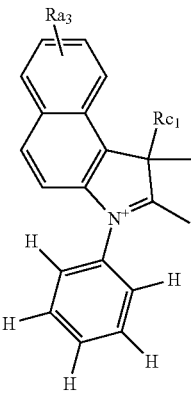

wherein $Ra_3$ is H, $SO_3^-$, sulphonamide or halogen; and $Rc_1$ is alkyl or substituted alkyl.

2. A compound according to claim 1 wherein Rb is alkyl or alkyl substituted with a carboxy or a sulfonic group.

3. A compound according to claim 1 wherein Rc1 or Rc2 is methyl, ethyl, propyl or —$(CH_2)_q SO_3^-$ where q is 1-6.

4. A compound according to claim 1 wherein the linking moiety is attached to Rb.

5. A compound according to claim 1 wherein the compound is attached to a nucleotide or oligonucleotide via Rb.

6. A nucleotide or oligonucleotide labelled with a compound according to claim 1.

7. A labelled nucleotide or oligonucleotide according to claim 6 wherein the label is attached via substituted alkyl group Rb.

8. A labelled nucleotide or oligonucleotide according to claim 6 wherein the label is attached to the C5 position of a pyrimidine base or the C7 position of a 7-deaza purine base through a linker moiety.

9. A labelled nucleotide or oligonucleotide according to claim 6, further comprising a 3' OH blocking group covalently attached to the ribose or deoxyribose sugar of the nucleotide.

10. A kit comprising two or more nucleotides wherein at least one nucleotide is a labelled nucleotide according to claim 6.

11. A kit according to claim 10 wherein two of the labelled nucleotides are excited using a single laser.

12. A kit according to claim 10 further comprising a second, third, and fourth nucleotide, each labelled with a different compound, wherein each compound has a distinct absorbance maximum and each of the compounds is distinguishable from the other three compounds.

13. A kit according to claim 10 wherein a first of four nucleotides is a labelled nucleotide and two of the compounds have a distinct absorbance maximum above 600 nm.

14. A method of sequencing comprising:
a) providing a nucleotide according to claim 6;
b) incorporating the nucleotide into the complement of an immobilized target polynucleotide; and
c) detecting the nucleotide incorporated in step b).

15. The method according to claim 14, wherein said detecting is performed on an automated sequencing instrument wherein said automated sequencing instrument comprises two light sources operating at different wavelengths.

16. A method of synthesising a compound according to claim 1 comprising:

a) providing one or more of the following starting material:
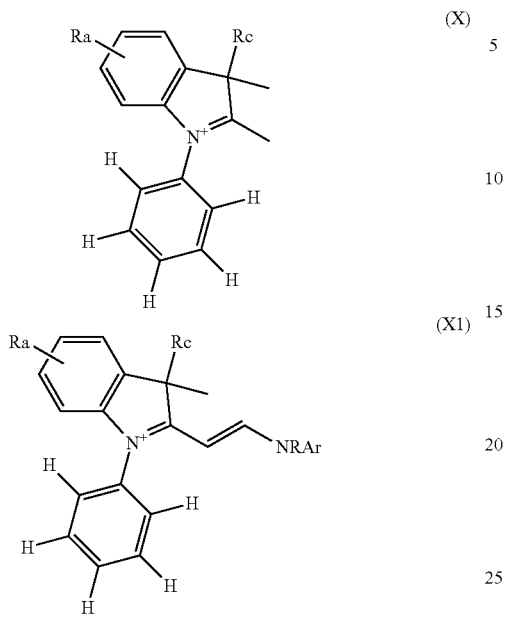
or a salt thereof wherein Ra is H, SO3-, sulfonamide, halogen, or a further ring fused to an adjacent carbon atom; and
b) performing a synthetic reaction with said starting material to obtain a compound according to claim 1.
\* \* \* \* \*